US007012693B2

(12) United States Patent
Mori et al.

(10) Patent No.: US 7,012,693 B2
(45) Date of Patent: Mar. 14, 2006

(54) SENSOR UTILIZING ATTENUATED TOTAL REFLECTION

(75) Inventors: Nobufumi Mori, Kaisei-machi (JP); Takeharu Tani, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 296 days.

(21) Appl. No.: 10/238,785

(22) Filed: Sep. 11, 2002

(65) Prior Publication Data

US 2003/0048453 A1    Mar. 13, 2003

(30) Foreign Application Priority Data

Sep. 12, 2001  (JP)  ............................. 2001/276227
Jun. 26, 2002  (JP)  ............................. 2002/186384

(51) Int. Cl.
*G01N 21/55* (2006.01)
(52) U.S. Cl. .................................................... 356/445
(58) Field of Classification Search ................. 356/445
See application file for complete search history.

(56) References Cited

U.S. PATENT DOCUMENTS 5,341,215 A * 8/1994 Seher .......................... 356/445
6,139,797 A * 10/2000 Suzuki et al. ................ 356/445

FOREIGN PATENT DOCUMENTS

| EP | 0 286 195 A2 | 10/1988 |
| EP | 0 517 930 A1 | 12/1992 |
| JP | 6-167443 | 6/1994 |
| WO | WO 00/22419 A1 | 4/2000 |

OTHER PUBLICATIONS

Spectral Research, vol. 47, No. 1, pp. 21-23 and 26-27.

* cited by examiner

*Primary Examiner*—HWA (Andrew) Lee
*Assistant Examiner*—Kara Geisel
(74) *Attorney, Agent, or Firm*—Sughrue Mion, PLLC

(57) ABSTRACT

A sensor comprising a light source for emitting a light beam, and a measuring chip. The measuring chip includes a dielectric block transparent to the light beam, a thin film layer formed on the dielectric block, and a liquid-sample holding mechanism for holding a liquid sample. The sensor also comprises an optical system for making the light beam enter the dielectric block at an angle of incidence so that a total internal reflection condition is satisfied at an interface between the dielectric block and the thin film layer. The sensor further comprises a photodetector for detecting the intensity of the light beam totally reflected at the interface, and a measuring section for measuring a state of attenuated total reflection, based on the result of detection obtained by the photodetector. The irradiation energy of the light beam at the interface is 100 mJ/mm² or less.

16 Claims, 10 Drawing Sheets

SENSOR UTILIZING ATTENUATED TOTAL REFLECTION

BACKGROUND OF THE INVENTION

1. Field of the Invention

The present invention relates to a sensor utilizing attenuated total reflection (ATR), such as a surface plasmon resonance sensor for quantitatively analyzing the properties of a substance in a liquid sample by utilizing surface plasmon excitation, and more particularly to a sensor utilizing ATR, equipped with a measuring chip which has a liquid-sample holding mechanism for holding a liquid sample.

2. Description of the Related Art

In metals, if free electrons are caused to vibrate in a group, a compression wave called a plasmon wave will be generated. The compression wave, generated in the metal surface and quantized, is called a surface plasmon.

There are various kinds of surface plasmon resonance sensors for quantitatively analyzing a substance in a liquid sample by taking advantage of a phenomenon that the surface plasmon is excited by light waves. Among such sensors, one employing the "Kretschmann configuration" is particularly well known (see, for example, Japanese Unexamined Patent Publication No. 6(1994)-167443).

The surface plasmon resonance sensor employing the aforementioned "Kretschmann configuration" is constructed basically of a measuring chip, a light source for emitting a light beam, an optical system, and photodetection means. The measuring chip is equipped with a dielectric block; a thin film layer consisting of a metal film formed on one surface of the dielectric block; and a liquid-sample holding mechanism for holding a liquid sample on the thin film layer. The dielectric block is formed, for example, into the shape of a prism. The optical system is used to make the light beam enter the dielectric block at various angles of incidence so that a condition for total internal reflection (TIR) is satisfied at the interface between the dielectric block and the thin film layer. The photodetection means measures the intensity of the light beam totally reflected at the interface, and detects the state of surface plasmon resonance, that is, the state of ATR.

To obtain various angles of incidence in the aforementioned manner, a relatively thin light beam is caused to strike the aforementioned interface at different angles of incidence, or a relatively thick light beam is caused to strike the interface convergently or divergently so that it includes components incident on the interface at various angles of incidence. In the former, the light beam whose reflection angle changes according to changes in the incidence angle thereof can be detected by a photodetector movable in synchronization with the reflection angle change, or by an area sensor extending along the direction in which the reflection angle changes. In the latter, the light beams reflected at various angles can be detected by an area sensor extending in the direction where all the reflected light beams can be received.

In the surface plasmon resonance sensor mentioned above, if a light beam strikes the thin film layer at a specific incidence angle $\theta_{sp}$ greater than a critical incidence angle at which total internal reflection (TIR) takes place, an evanescent wave having an electric field distribution is generated in a liquid sample in contact with the thin film layer. The evanescent wave excites the above-described surface plasmon at the interface between the thin film layer and the liquid sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light totally reflected at the interface between the dielectric block and the thin film layer drops sharply. This sharp intensity drop is generally detected as a dark line by the above-described photodetection means.

Note that the aforementioned resonance occurs only when an incident light beam is a p-polarized light beam. Therefore, in order to make the resonance occur, there is a need to make settings in advance so that a light beam can strike the aforementioned interface as a p-polarized light beam.

If the wave number of the surface plasmon is found from the specific incidence angle $\theta_{sp}$ at which attenuated total reflection (ATR) takes place, the dielectric constant of a liquid sample to be analyzed can be calculated by the following Equation:

$$K_{sp}(\omega) = \frac{\omega}{c}\sqrt{\frac{\varepsilon_m(\omega)\varepsilon_s}{\varepsilon_m(\omega)+\varepsilon_s}}$$

where $K_{sp}$ represents the wave number of the surface plasmon, $\omega$ represents the angular frequency of the surface plasmon, c represents the speed of light in vacuum, and $\in_m$ and $\in_s$ represent the dielectric constants of the thin film layer and the liquid sample, respectively.

If the dielectric constant $\in_s$ of a liquid sample is found, the concentration of a specific substance in the liquid sample is found based on a predetermined calibration curve, etc. As a result, the dielectric constant of the liquid sample, that is, the properties of the liquid sample related to the refractive index thereof can be quantitatively analyzed by finding the specific incidence angle $\theta_{sp}$ at which the intensity of the reflected light at the interface drops sharply.

In addition, a leaky mode sensor is known as a similar sensor making use of ATR (for example, see "Spectral Research" Vol. 47, No. 1 (1998), pp. 21 to 23 and pp. 26 to 27). This leaky mode sensor is constructed basically of a measuring chip, a light source for emitting a light beam, an optical system, and photodetection means. The measuring chip is equipped with a dielectric block; a thin film layer consisting of a cladding layer formed on one surface of the dielectric block and an optical waveguide layer formed on the cladding layer; and a liquid-sample holding mechanism for holding a liquid sample on the thin film layer. The dielectric block is formed, for example, into the shape of a prism. The optical system is used to make the light beam enter the dielectric block at various angles of incidence so that a condition for total internal reflection (TIR) is satisfied at the interface between the dielectric block and the cladding layer. The photodetection means measures the intensity of the light beam totally reflected at the interface, and detects the excitation state of a waveguide mode, that is, the state of ATR.

In the leaky mode sensor of the aforementioned construction, if a light beam strikes the cladding layer through the dielectric block at incidence angles greater than a critical incidence angle at which total internal reflection (TIR) takes place, the light beam is transmitted through the cladding layer. Thereafter, in the optical waveguide layer formed on the cladding layer, only light with a specific wave number, incident at a specific incidence angle, propagates in a waveguide mode. If the waveguide mode is excited in this manner, most of the incident light is confined within the optical waveguide layer, and consequently, ATR occurs in which the intensity of light totally reflected at the aforementioned interface drops sharply. Since the wave number of the light propagating through the optical waveguide layer depends upon the refractive index of the liquid sample on the optical waveguide layer, the refractive index of the liquid sample and the properties of the liquid sample related to the refractive index can be analyzed by finding the above-described specific incidence angle $\theta_{sp}$ at which ATR takes place.

As described in Japanese Patent Application No. 2001-047885, there are cases where in the field of pharmaceutical research, the above-mentioned surface plasmon resonance sensor and leaky mode measuring sensor are employed in the research of the interaction between a desired sensing substance and a liquid sample. For instance, the sensors are employed in the measurement of interactions, such as a bond between a sensing substance and a specific substance which is contained in a liquid sample, a dissociation of a bonded substance into a specific substance contained in a liquid sample, etc. Such interactions include protein-protein interactions, DNA-protein interactions, sugar-protein interactions, protein-peptide interactions, lipid-protein interactions, bonds between chemical substances, and so on.

In addition, there are cases where the above-mentioned surface plasmon resonance sensor and leaky mode measuring sensor are used in a random screening method for detecting a specific substance that bonds to a sensing substance. In this case, a sensing substance is fixed on the aforementioned thin film layer. Then, a liquid sample with various target substances in a solvent is added to the sensing substance, and each time a predetermined time elapses, the state of ATR is measured.

If a target substance in the liquid sample bonds to the sensing substance, the refractive index of the sensing substance changes with the lapse of time by the bond therebetween. Therefore, the state of ATR is measured at predetermined time intervals and it is measured whether there is a change in the state of ATR. In this manner, it can be judged whether there is a bond between the target substance and the sensing substance, that is, whether the target substance is a specific substance that bonds with the sensing substance. The combination of the specific substance and the sensing substance includes a combination of an antigen and an antibody and a combination of an antibody and an antibody. Specifically, a rabbit antihuman immunoglobulin G (IgG) antibody may be fixed to a measuring chip as a sensing substance, and a human IgG antibody may be employed as a specific substance.

In prior art sensors utilizing ATR which have been proposed, a liquid sample is first supplied to a cup-shaped or dish-shaped measuring chip which has a thin film layer on the bottom surface thereof. Then, a light beam is caused to strike the dielectric block of the measuring chip so that a condition for total internal reflection is obtained at the interface between the dielectric block and the thin film layer. Next, the intensity of the light beam totally reflected at the interface is detected. Based on the result of detection, the state of ATR is measured. To enhance accuracy in detection of the light intensity, it is desirable to increase the irradiation energy of the light beam that strikes the interface. On the other hand, if the irradiation energy of the light beam is increased, the temperature of the liquid sample held on the thin film layer will rise and therefore the refractive index will change. Because of this, there is a problem that accuracy in measurement of the state of ATR will be reduced, or in the case of a great rise in temperature, measurements will become impossible. These problems have not been examined in the above-described prior art sensors that utilize ATR.

SUMMARY OF THE INVENTION

The present invention has been made in view of the circumstances mentioned above. Accordingly, it is the primary object of the present invention to provide a sensor, utilizing ATR, which is capable of preventing a rise in temperature of a liquid sample, thereby enhancing accuracy in measurement of the state of ATR.

To achieve this end and in accordance with the present invention, there is provided a sensor which utilizes attenuated total reflection. The sensor comprises a light source for emitting a light beam, and a measuring chip. The measuring chip includes a dielectric block transparent to the light beam, a thin film layer formed on one surface of the dielectric block, and a liquid-sample holding mechanism for holding a liquid sample on the thin film layer. The sensor also comprises an optical system for making the light beam enter the dielectric block at an angle of incidence so that a total internal reflection condition is satisfied at an interface between the dielectric block and the thin film layer. The sensor further comprises photodetection means for detecting intensity of the light beam totally reflected at the interface, and measurement means for measuring a state of attenuated total reflection, based on the result of detection obtained by the photodetection means. The irradiation energy of the light beam at the interface is 100 mJ/mm$^2$ or less.

Such a sensor includes the aforementioned surface plasmon resonance sensor which employs a metal film as the above-described thin film layer, and the leaky mode sensor which employs a layer, which consists of a cladding layer formed on one surface of a dielectric block and an optical waveguide layer formed on the cladding layer, as the above-described thin film layer.

The irradiation energy of the light beam may be 50 mJ/mm$^2$ or less. It may also be 10 mJ/mm$^2$ or less.

In the case where a sensing substance which interacts with the aforementioned liquid sample is placed on the above-described thin film layer, the above-described measurement means may be constructed to measure a temporal change in the state of attenuated total reflection (ATR), based on a plurality of detection results obtained at predetermined time intervals by the photodetection means. Such a liquid sample which interacts with the sensing substance includes various liquid samples which contain various target substances in a solvent solution such as water, a physiological saline solution, and a 10% dimethyl sulfoxide solution.

The sensor of the present invention may further comprise a shutter disposed between the light source and the dielectric block, and timing control means for controlling the timing at which an operation of detection in the photodetection means is performed or the timing at which an operation of measurement in the measurement means is performed so that they are in synchrony with the opening operation of the shutter.

In addition, the sensor of the present invention may employ various methods of detecting the intensity of the light beam totally reflected at the aforementioned interface by photodetection means to measure the state of attenuated total reflection (ATR). For example, a light beam may be caused to strike the aforementioned interface at various angles of incidence so that a total internal reflection condition is satisfied at the interface. Then, the intensity of the light beam totally reflected at the interface is measured at each position corresponding to each incidence angle. Based on the intensity, the position (angle) of a dark line generated due to ATR is detected. In this way, the state of ATR may be measured.

In addition, a light beam with a plurality of wavelengths may be caused to enter a measuring chip at angles of incidence so that a total internal reflection condition is satisfied at the interface. Then, the intensity of the light beam totally reflected at the interface is measured for each wavelength. In this way, by measuring the degree of ATR for each wavelength, the state of ATR may be measured (see D. V. Noort, K. Johansen, C. -F. Mandenius, Porous Gold in Surface Plasmon Resonance Measurement, EUROSENSORS XIII, 1999, pp. 585–588).

Furthermore, the state of ATR may be measured by making a light beam enter a measuring chip at an angle of incidence so that a total internal reflection condition is satisfied at the aforementioned interface, then splitting the light beam into two light beams before the light beam strikes the interface, then causing one of the two light beams to interfere with the other light beam totally reflected at the interface, and measuring the intensity of the light beam after the interference (see P. I. Nikitin, A. N. Grigorenko, A. A. Beloglazov, M. V. Valeiko, A. I. Savchuk, O. A. Savchuk, Surface Plasmon Resonance Interferometry for Micro-Array Biosensing, EUROSENSORS XIII, 1999, pp. 235–238).

In the sensor of the present invention which utilizes ATR, a light beam with an irradiation energy of 100 $mJ/mm^2$ or less strikes the interface between the dielectric block and thin film layer of a measuring chip. The intensity of the light beam totally reflected at the interface is detected by photodetection means, and the state of ATR is measured. Therefore, a rise in temperature of the liquid sample held on the thin film layer is prevented and accuracy in measurement of the state of ATR can be enhanced.

For instance, in the case of measuring a bond between a sensing substance and a target substance which is contained in a liquid sample, as described above, the molecular weight of the target substance is typically 200 or greater. For example, in the case where the target substance is used in an orally administered medication, etc., the molecular weight is typically 200 to 1000. If the target substance is protein, the molecular weight is typically 1000 or greater. FIG. 10 shows the relationship between the irradiation energy of a light beam at the interface of a measuring chip and a change in refractive index (converted to terms of molecular weight) of a liquid sample due to the irradiation of the light beam. From the figure it is found that when a light beam with an irradiation energy of 200 $mJ/mm^2$ is irradiated, the change in refractive index of a liquid sample is 2000 or greater when converted to molecular weight. In the case where a change in refractive index is 2000 or greater in molecular weight when the molecular weight of a target substance is about 1000, the result of measurements is unreliable.

In the case where a light beam with an irradiation of 100 $mJ/mm^2$ or less is irradiated, a change in refractive index of a liquid sample due to irradiation of the light beam is about 200 when converted to molecular weight, as shown in FIG. 10. If a target substance in a liquid sample is protein, the molecular weight is typically 1000 or greater. Therefore, in the case where a change in refractive index is 200 or less converted to molecular weight, the accuracy of measurement in a temporal change in the state of ATR will not be reduced. For example, when making a judgement of whether a target substance is a specific substance which bonds a sensing substance, the accuracy of judgement will not be reduced.

In the case where a light beam with an irradiation energy of 50 $mJ/mm^2$ or less is irradiated to the interface between the dielectric block and thin film layer of a measuring chip, and the intensity of the light beam totally reflected at the interface is detected by photodetection means to measure the state of ATR, a rise in temperature of the liquid sample held on the thin film layer is further prevented and accuracy in measurement of the state of ATR can be further enhanced. That is, when a light beam with an irradiation energy of 50 $mJ/mm^2$ or less is irradiated, a change in refractive index of a liquid sample due to irradiation of the light beam is 100 or less converted to molecular weight, as shown in FIG. 10. Therefore, if the molecular weight of a target substance in a liquid sample is 200 or greater, a temporal change in the state of ATR can be measured even if there is a change in refractive index of 100 or less converted to molecular weight. That is, it can be judged whether a target substance is a specific substance which bonds a sensing substance.

In the case where a light beam with an irradiation energy of 10 $mJ/mm^2$ or less is irradiated to the interface between the dielectric block and thin film layer of a measuring chip, and the intensity of the light beam totally reflected at the interface is detected by photodetection means to measure the state of ATR, a rise in temperature of the liquid sample held on the thin film layer is further prevented and accuracy in measurement of the state of ATR can be further enhanced. That is, when a light beam with an irradiation energy of 10 $mJ/mm^2$ or less is irradiated, a change in refractive index of a liquid sample due to irradiation of the light beam is 50 or less in molecular weight, as shown in FIG. 10. Therefore, if the molecular weight of a target substance in a liquid sample is 200 or greater, it can be judged whether there is a bond between the target substance and the sensing substance, even if there is a change in refractive index of 50 or less converted to molecular weight. That is, it can be judged whether a target substance is a specific substance which bonds a sensing substance. The change in refractive index has little influence on the accuracy of judgement.

When the sensor of the present invention includes the aforementioned shutter and the aforementioned timing control means for synchronizing the detection by the photodetection means or the measurement by the measuring means with the opening operation of the shutter, the irradiation energy of a light beam at the interface between the dielectric block and the thin film layer can be accurately controlled. In addition, if the detection of the light intensity or measurement of the state of ATR is performed in synchronization with the opening operation of the shutter, that is, the timing at which the light beam is irradiated to the interface, then detection signals during periods in which the light beam 30 is not irradiated can be prevented from having influence on the result of measurements as noise. Thus, the reliability of the measurement result is enhanced.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
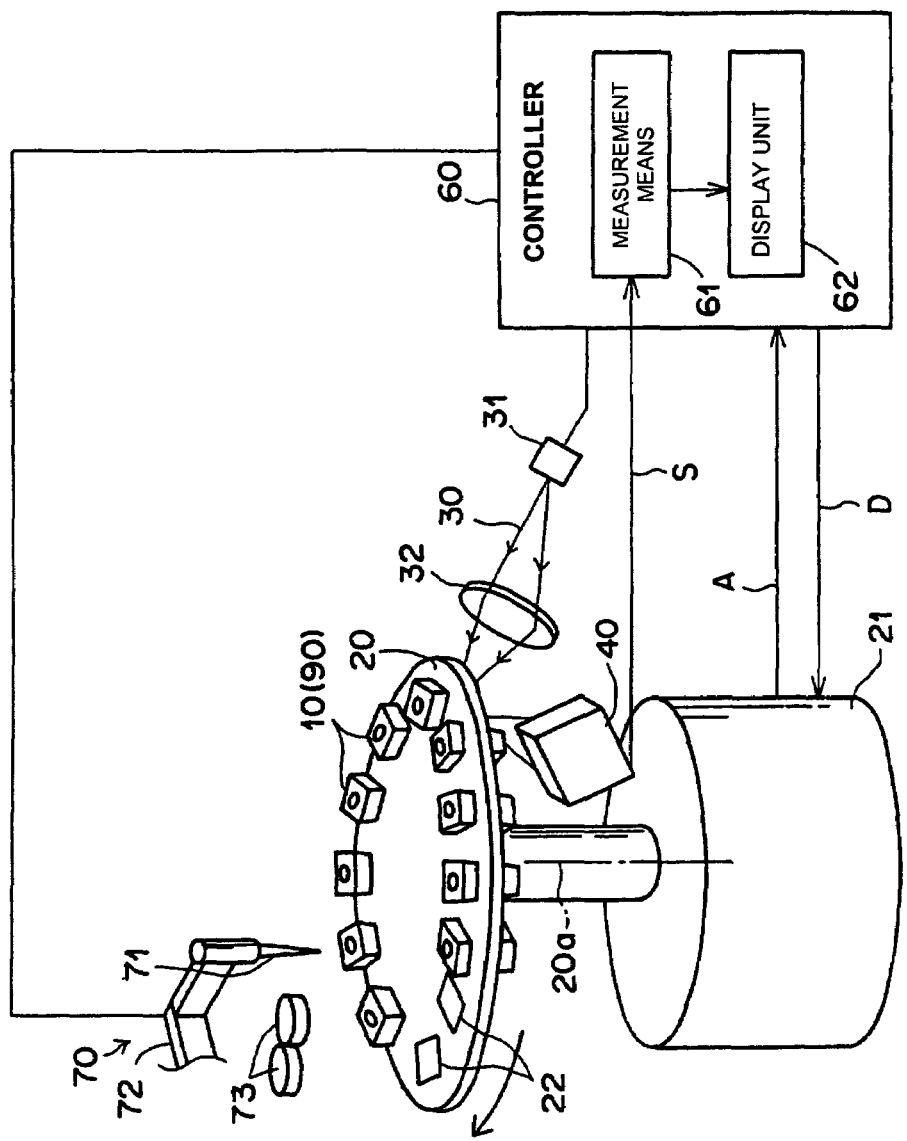
FIG. 1 is a perspective view showing a surface plasmon resonance sensor constructed in accordance with a first embodiment of the present invention.
Figure 2:
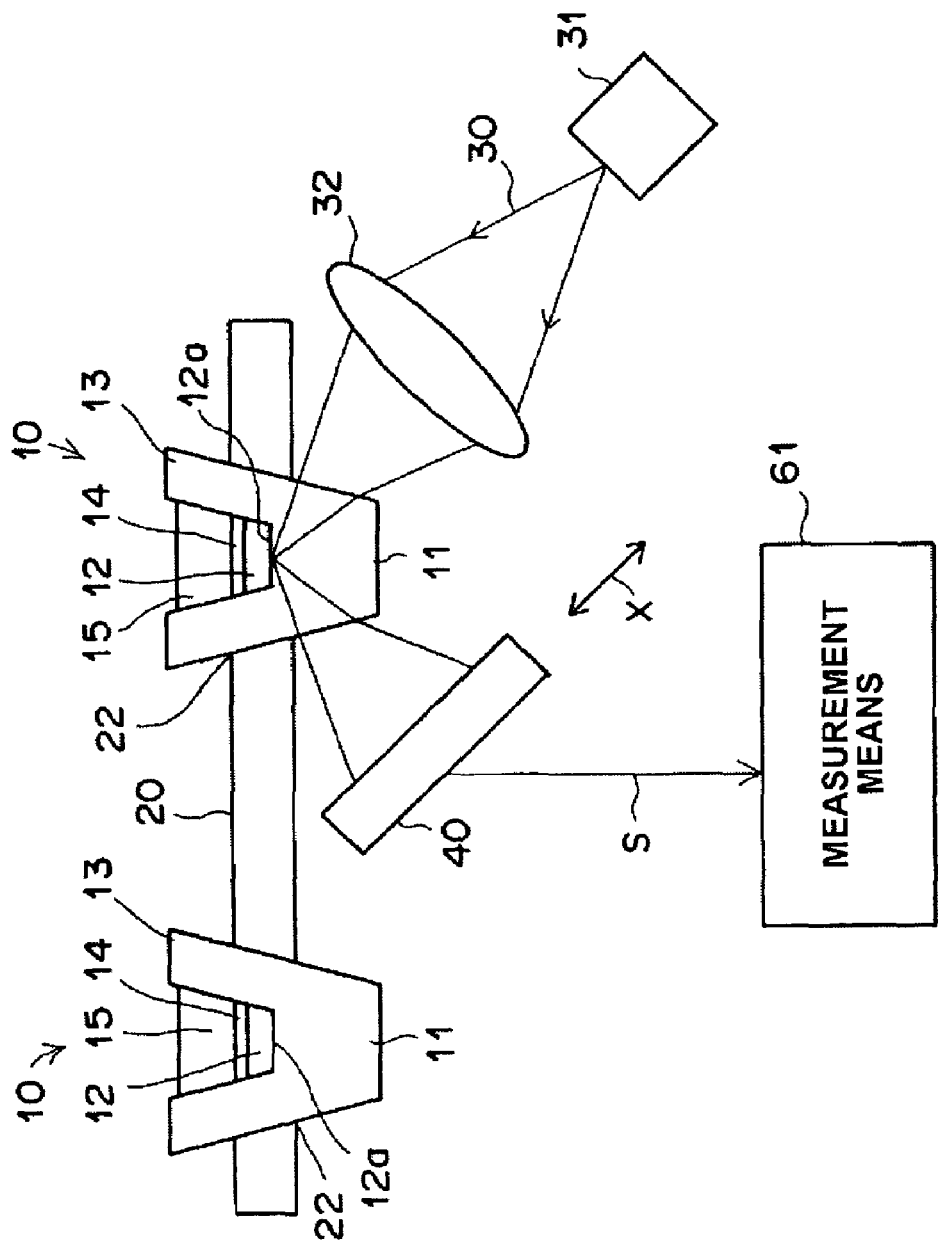
FIG. 2 is a side view of the surface plasmon resonance sensor shown in FIG. 1.

Referring now to the drawings, which are for purposes of illustrating preferred embodiments of the present invention only, and not for purposes of limiting the same, FIGS. 1 and 2 depict a surface plasmon resonance sensor constructed in accordance with a first embodiment of the present invention. In the surface plasmon resonance sensor, a change in the specific angle $\theta_{sp}$ where ATR occurs due to surface plasmon resonance is measured to judge a bond between a sensing substance and a target substance. That is, it is judged whether a target substance is a specific substance.

The surface plasmon resonance sensor of the first embodiment has a plurality of measuring chips 10, a turntable 20 for supporting the measuring chips 10, and turntable drive means (movement means) 21 for rotating the turntable 20 intermittently. The surface plasmon resonance sensor also has a laser light source (e.g., a semiconductor laser) 31 for emitting a measuring light beam (e.g., a laser beam) 30, a condenser lens 32 constituting an optical incidence system, and a photodetector 40. The surface plasmon resonance sensor further has a controller 60 for controlling both the laser light source 31 and the turntable drive means 21, and a liquid-sample supply mechanism 70. In response to a signal S output from the photodetector 40, the controller 60 carries out a process, which will be described later.

The measuring chip 10 is constructed of a dielectric block 11 and a metal film 12, as shown in FIG. 2. The dielectric block 11 is formed, for example, into a generally truncated quadrangular pyramid shape. The metal film 12 is formed on one surface (the top surface in the figure) of the dielectric block 11 and is made, for example, of gold, silver, copper, aluminum, etc.

The dielectric block 11 is made, for example, of transparent resin, etc. The dielectric block 11 has a liquid-sample holding portion 13 formed by raising the edges around the periphery of the metal film 12 which serves as a liquid-sample holding mechanism for storing a liquid sample 15.

The dielectric block 11 in the first embodiment includes a sensing substance 14, which is fixed on the metal film 12. The sensing substance 14 will be described later.

The turntable 20 has a plurality of through holes 22 in which the measuring chips 10 are fitted. In the first embodiment, 12 (twelve) through holes 22 are provided on a circle at equiangular intervals with respect to the rotational axis 20a of the turntable 20. The measuring chips 10 are exchangeable with respect to the turntable 20. The turntable drive means 21 is constructed of a stepping motor, etc. This turntable drive means 21 is used for rotating the turntable 20 intermittently at intervals of an angle equal to the pitch between the through holes 22.

The condenser lens 32, as shown in FIG. 2, collects the light beam 30 and makes the light beam 30 enter the dielectric body 11 in a convergent state so that various angles of incidence are obtained with respect to the interface 12a between the dielectric block 11 and the metal film 12. The incidence angle range includes incidence angles at which a total internal reflection condition for the light beam 30 is satisfied at the interface 12a, and at which surface plasmon resonance can occur.

Note that the light beam 30 needs to strike the interface 12a as a p-polarized light beam. For this reason, it is necessary to dispose the laser light source 31 so that the polarization direction thereof becomes a predetermined direction. In addition, the polarization direction of the light beam 30 may be controlled with a wavelength plate, a polarizing plate, etc. The laser light source 31 and the condenser lens 32 are configured such that when a measurement is made, the irradiation energy of the light beam at the interface 12a is 50 mJ/mm$^2$.

The photodetector 40 is a photodiode array consisting of a great number of photodiodes. The photodiodes are arranged in a row in the direction of arrow X in FIG. 2.

The controller 60 receives an address signal A which represents a position at which rotation of the turntable drive means 21 is stopped, from the turntable drive means 21. Based on a predetermined sequence, the controller 60 also outputs a drive signal D to actuate the turntable drive means 21. Furthermore, the controller 60 is equipped with measurement means 61 to which the output signal S from the aforementioned photodetector 40 is input, and a display unit 62 to which an output signal from the measurement means 61 is output.

Figure 3:
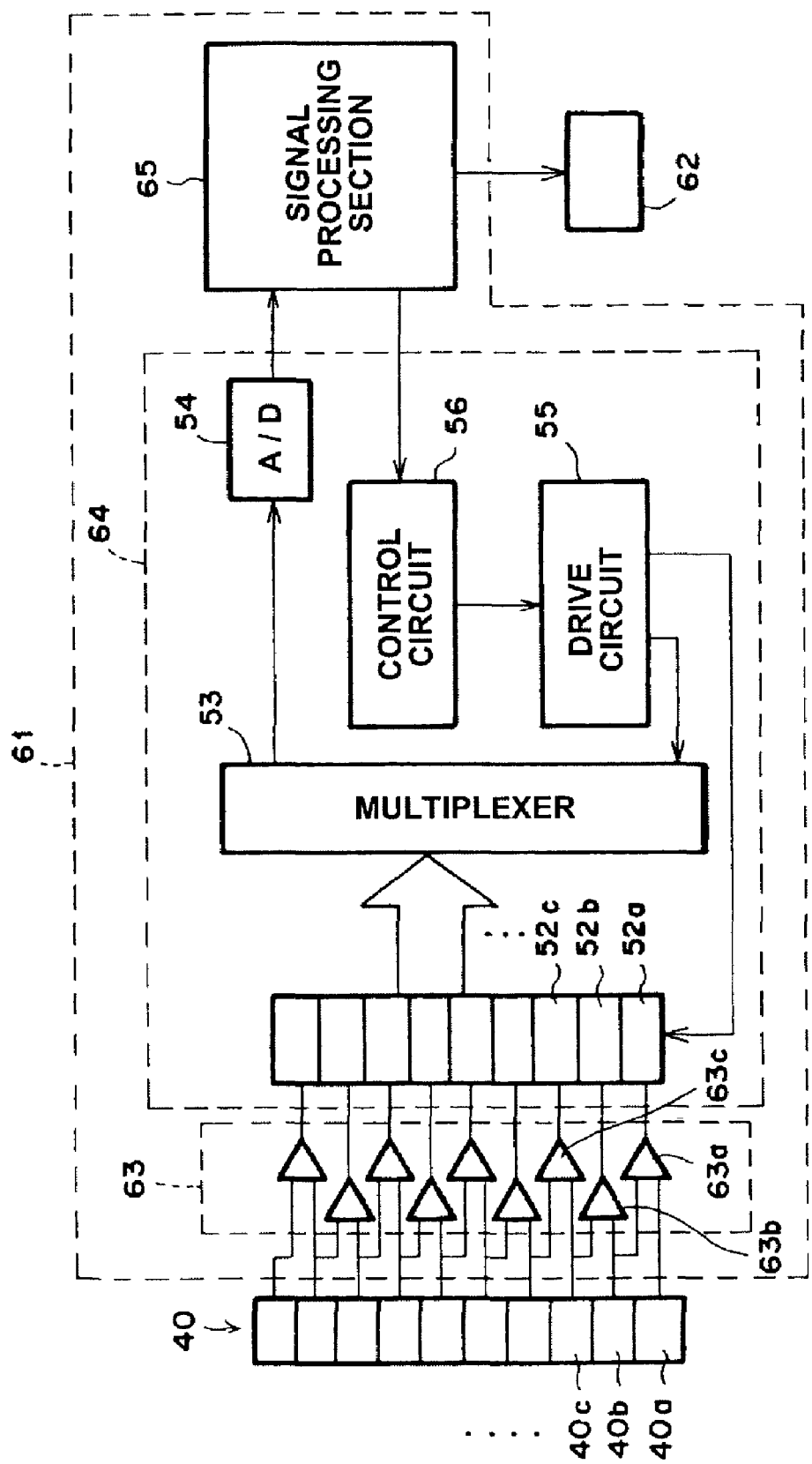
FIG. 3 is a block diagram of measurement means employed in the surface plasmon resonance sensor of FIG. 1.

As shown in FIG. 3, the measurement means 61 is constructed of a differential amplifier array 63 connected to the photodetector 40; a driver 64; and a signal processing section 65 consisting of a computer system, etc.

The driver 64 includes sample holding circuits 52a, 52b, 52c, . . . for holding outputs of the differential amplifiers 63a, 63b, 63c, . . . of the differential amplifier array 63; a multiplexer 53 to which the outputs of the sample holding circuits 52a, 52b, 52c, . . . are input; and an A/D converter 54 for digitizing the output of the multiplexer 53 and then inputting the digitized output to the signal processing section 65. The driver 64 further includes a drive circuit 55 for driving the multiplexer 53 and the sample holding circuits 52a, 52b, 52c, . . . ; and a controller 56 for controlling operation of the drive circuit 55 in response to a control signal from the signal processing section 65.

The liquid-sample supply mechanism 70 consists of a pipette 71 for suctioning and holding a predetermined amount of a liquid sample, and means 72 for moving the pipette 71. The liquid-sample supply mechanism 70 suctions and holds a liquid sample through the pipette 71 from a liquid-sample container 73 situated at a predetermined position, and drops the liquid sample into the liquid-sample holding mechanism 13 of the measuring chip 10, which is at a predetermined stop position on the turntable 20.

A description will hereinafter be given of how a change in the specific angle $\theta_{sp}$ where ATR occurs due to surface plasmon resonance is measured by the surface plasmon resonance sensor of the first embodiment. Initially, before making actual measurements, a plurality of kinds of liquid samples 15, consisting of a target substance and a solvent, are prepared. A number of measuring chips 10 that corresponds to the number of the different liquid samples are also prepared. Generally, a sensing substance that is fixed to the measuring chip 10 varies from one operator to the next. Because of this, an operator fixes the sensing substance 14 to the measuring chip 10 to which the sensing substance 14 has not been fixed.

For instance, in the case where the sensing substance 14 is streptoavidin that is a sort of protein, an ethanol solution with 1 mM of DDA (dithio dibutyric acid) is stored in the measuring chips 10 for 24 hours under an atmosphere of ethanol saturated steam, and the measuring chips 10 are cleaned with an ethanol solution. Then, a phosphate buffer solution (PBS) with 0.2 M of 1-ethyl-3-(3-dimethtlamino-propyl)carbodiimide (EDC) and 0.1 M of N-hydrooxysuc-cinimide (NHS) is stored in the measuring chips 10 for 10 minutes, and the measuring chips 10 are cleaned with PBS. Thereafter, 10 µg/mL of streptoavidin is stored in the measuring chips 10 for 10 minutes, and the measuring chips 10 are cleaned with PBS. Next, ethanolamine is stored for 5 minutes and blocking is performed. The measuring chips 10 are cleaned with PBS, and a 1% bovine serum albumin (BSA) solution which is a stabilizer is stored for 10 minutes and the measuring chip 10 are again cleaned with PBS. In this manner, the measuring chips 10 with streptoavidin fixed as a sensing substance are prepared. In general, these measuring chips 10 are arranged in a 96-hole cassette (not shown).

The liquid samples 15 are prepared by dissolving various target substances in a solvent. The various target substances have a molecular weight of 200 or greater, while the solvent uses a PBS containing a 0.1% BSA solution (hereinafter referred to as 0.1% BSA.PBS: a kind of physiological saline solution).

Prior to measurement, the above-described sensing substance 14 is fixed and the measuring chips 10 arranged in the 96-hole cassette (not shown) are disposed in sequence on the turntable 20 by a measuring-chip moving mechanism (not shown).

When the turntable 20 is rotated and the measuring chip 10 is moved to the position where the liquid-sample supply mechanism 70 is provided, the liquid sample 15 is supplied to the liquid-sample holding portion 13 of the measuring chip 10 by the liquid-sample supply mechanism 70. If the turntable 20 is further rotated, the measuring chip 10 is moved to a measuring position where the above-mentioned light beam 30 enters the dielectric block 11 (for example, the position of the measuring chip 10 on the right side in FIG. 2). If the measuring chip 10 is held at the measuring position, the laser light source 31 is driven in response to a signal from the controller 60. As previously described, the light beam 30 emitted from the laser light source 31 strikes the interface 12a between the dielectric block 11 and the metal film 12 in a convergent state. As set forth above, the irradiation energy of the light beam 30 at the interface 12a is 50 mJ/mm² or less. The light beam 30 totally reflected at the interface 12a is detected by the photodetector 40.

The photodetector 40 in the first embodiment is a photodiode array consisting of a plurality of photodiodes 40a, 40b, 40c, . . . juxtaposed in a row. As shown in FIG. 2, the direction in which the photodiodes are juxtaposed is approximately perpendicular to the traveling direction of the light beam 13. Therefore, the components of the light beam 13 satisfying total internal reflection at various angles at the interface 12a are received by the different photodiodes 40a, 40b, 40c, . . . , respectively.

The outputs of the photodiodes 40a, 40b, 40c, . . . are input to the differential amplifiers 63a, 63b, 63c, . . . of the differential amplifier array 63. The outputs of two adjacent photodiodes are input to the common differential amplifier. Therefore, the outputs of the differential amplifiers 63a, 63b, 63c, . . . represent values obtained by differentiating the output signals of the photodiodes 40a, 40b, 40c, . . . in the direction where the photodiodes are juxtaposed.

The outputs of the differential amplifiers 63a, 63b, 63c, . . . are respectively held at predetermined timings by the sample holding circuits 52a, 52b, 52c, . . . and are input to the multiplexer 53. The multiplexer 53 inputs the held outputs of the differential amplifiers 63a, 63b, 63c . . . to an A/D converter 54 in a predetermined order. The A/D converter 54 digitizes these outputs and inputs them to the signal processing section 65.

Figure 4A:
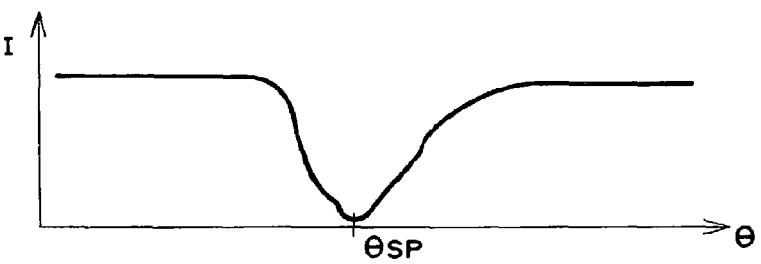
FIGS. 4A, 4B, and 4C are diagrams showing the relationship between the incidence angle of a light beam and the intensity of the light beam detected by a photodetector, and the relationship between the incidence angle of the light beam and the differentiated value of a light-intensity detection signal.

FIG. 4A shows the relationship between the incidence angle θ of the light beam 13 with respect to the interface 12a and the above-mentioned light intensity I. Light, incident at a specific angle $\theta_{sp}$ on the interface 12a between the metal film 12 and the sample 11, excites the above-described surface plasmon at the interface 12a. Because of this, for the light incident at the specific angle $\theta_{sp}$, the intensity I of the reflected light drops sharply. That is, the specific incidence angle $\theta_{sp}$ is an angle of incidence at which attenuated total reflection (ATR) occurs. The minimum value for the intensity I of the reflected light occurs at the specific incidence angle $\theta_{sp}$. The sharp drop of the intensity I of the reflected light is observed as a dark line in the reflected light.

Figure 4B:
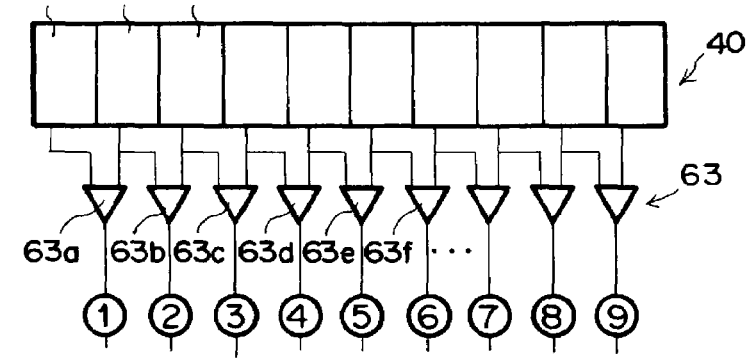

FIG. 4B shows the direction in which the photodiodes 40a, 40b, 40c, . . . are juxtaposed. As described previously, the positions of the photodiodes, juxtaposed perpendicular to the reflected light, correspond to the above-mentioned incidence angles θ.

Figure 4C:
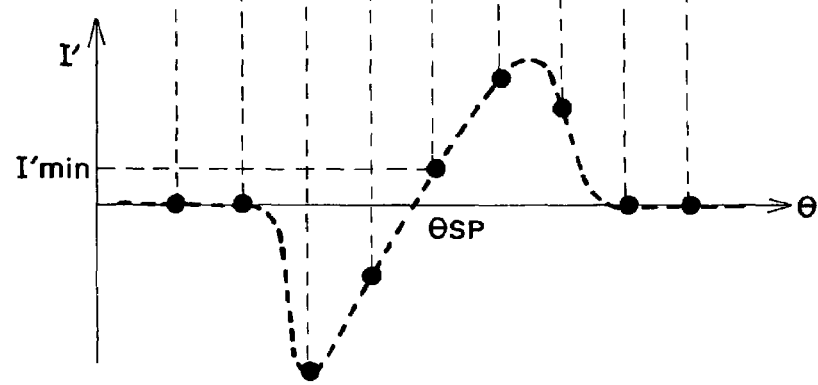

FIG. 4C shows the relationship between the positions of the juxtaposed photodiodes 40a, 40b, 40c, . . . (i.e., the incidence angles θ) and the outputs I' of the differential amplifiers 63a, 63b, 63c, . . . (i.e., differentiated values of reflected-light intensities I).

Based on the differentiated value I' input from the A/D converter 54, the signal processing section 65 selects a differential amplifier (e.g., the differential amplifier 63e in FIG. 4) whose output is closest to a differentiated value I'=0 corresponding to the aforementioned incident angle $\theta_{sp}$, from among the differential amplifiers 63a, 63b, 63c, . . . . The differentiated value I' output from the selected differential amplifier is displayed on the display unit 62. When there is present a differential amplifier which is outputting a differentiated value I'=0, it is a matter of course that that differential amplifier is selected. Next, the turntable 20 is rotated intermittently by the turntable drive means 21. Thereafter, each time a predetermined time elapses, the differentiated value I' output from the selected differential amplifier 63e is displayed on the display unit 62.

If the dielectric constant or refractive index of the sensing substance 14 in contact with the metal film 12 of the measuring chip 10 (see FIG. 2) changes so that the curve in FIG. 4A is horizontally moved, the differentiated value I' is increased or decreased according to the horizontal movement. Therefore, by continuously measuring the differentiated value I' with the lapse of time, a change in refractive index of the sensing substance 14 in contact with the metal film 12 can be detected.

If a target substance in the liquid sample 15 is a substance which bonds with the sensing substance 14, the refractive index of the sensing substance 14 changes according to the bond therebetween. Therefore, by continuously measuring the differentiated value I', the bond between the target substance ad the sensing substance 14 can be detected. Based on the result of measurement, it can be judged whether the target substance in the liquid sample 15 is a specific substance which bonds with the sensing substance 14.

That is, if the value of the differentiated value I' changes, it can be judged that the refractive index of the sensing substance 14 has changed. That is, it can be judged that a target substance in the liquid sample 15 is a substance which bonds the sensing substance 14. When there is no change in the value of the differentiated value I', it can be judged that the target substance is not a substance which bonds the sensing substance 14.

In the present embodiment, the irradiation energy of the light beam 30 which is irradiated to the interface 12a of the measuring chip 10 is 50 mJ/mm2 at the interface 12a, as previously described. Therefore, a change in refractive index of the liquid sample 15 due to irradiation of the light beam 30 comes to about 100 when converted to molecular weight. Since the molecular weight of a target substance in the liquid sample 15 is 200 or greater, the bond between the target substance and the sensing substance 14 can be accurately measured even if a change in refractive index of about 100 converted to molecular weight occurs as an error. Therefore, it can be judged whether there is a bond between the target substance and the sensing substance 14. That is, it can be accurately judged whether the target substance is a specific substance which bonds with the sensing substance 14.

If the irradiation energy of the light beam 30 at the interface 12a is 10 mJ/mm$^2$ or less, a change in refractive index of the liquid sample 15 due to irradiation of the light beam 30 is 50 or less when converted to molecular weight and therefore a more accurate judgement can be made. However, there is a need to employ equipment that has good detection accuracy as the photodetector 40, and in addition, it is necessary to consider elimination of noise.

If the target substance is a substance whose molecular weight is 1000 or greater, such as protein, etc., a bond between the sensing substance 14 and the target substance can be accurately measured even if the irradiation energy of the light beam 30 at the interface 12a is increased up to 100 mJ/mm$^2$. Therefore, an inexpensive device can be employed.

In addition, a construction has been adopted wherein the turntable 20 with a plurality of measuring chips 10 is rotated, and the measuring chips 10 can be held at a predetermined position relative to the condenser lens 32 and photodetector 40 in a sequential manner. Therefore, the differentiated values of the measuring chips 10 can be measured sequentially by rotation of the turntable 20, and it becomes possible to measure a great number of measuring chips 10 in a short time.

In the embodiment described above, the dielectric body 11, metal film 12, and liquid-sample holding portion 13 are integrally formed as the measuring chip 10. However, the measuring chip 10 is not limited to this. The metal film 12 and the liquid-sample holding portion 13 may be formed as an integral body that is exchangeable with respect to the dielectric block 11.

Furthermore, a construction may be adopted wherein the amount of the light beam 30 to be emitted from the laser light source 31 is controlled, and the irradiation energy of the light beam 30 at the interface 12a can be switched among the three steps of 100 mJ/mm$^2$, 50 mJ/mm$^2$, and 10 mJ/mm$^2$. The operator can select the most appropriate one of them in consideration of the molecular weight of a target substance, detection sensitivity of the photodetector 40, etc.

Figure 5:
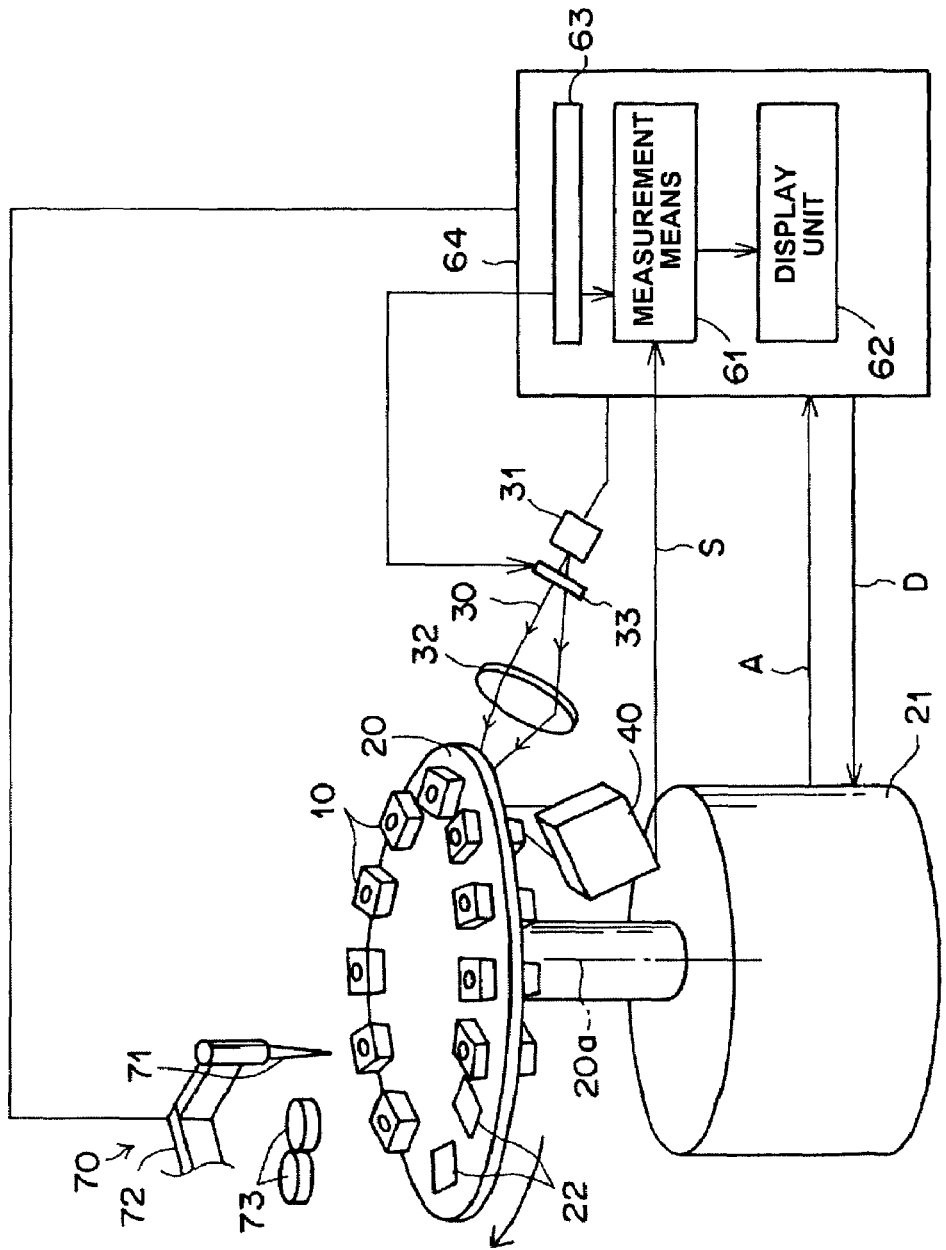
FIG. 5 is a perspective view showing a surface plasmon resonance sensor constructed in accordance with a second embodiment of the present invention.
Figure 6:
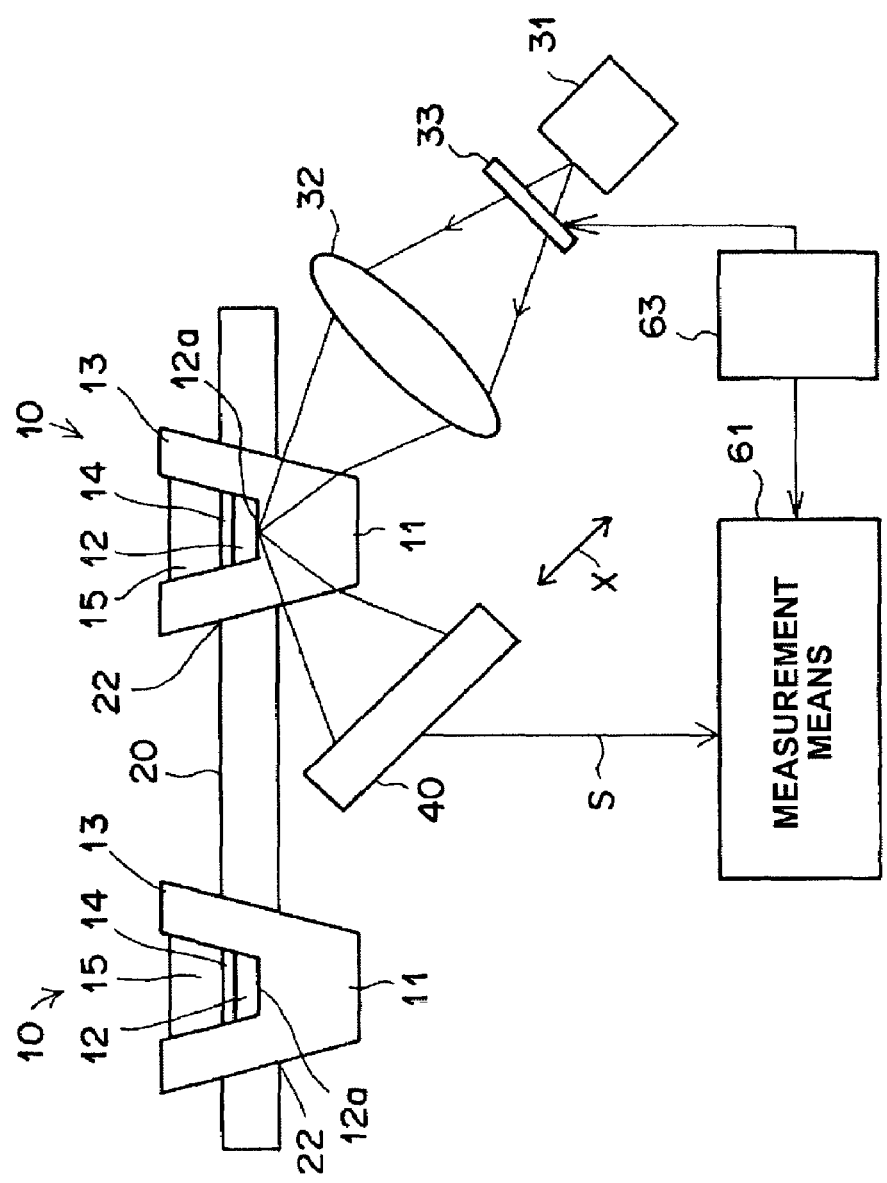
FIG. 6 is a side view of the surface plasmon resonance sensor shown in FIG. 5.
Figure 7:
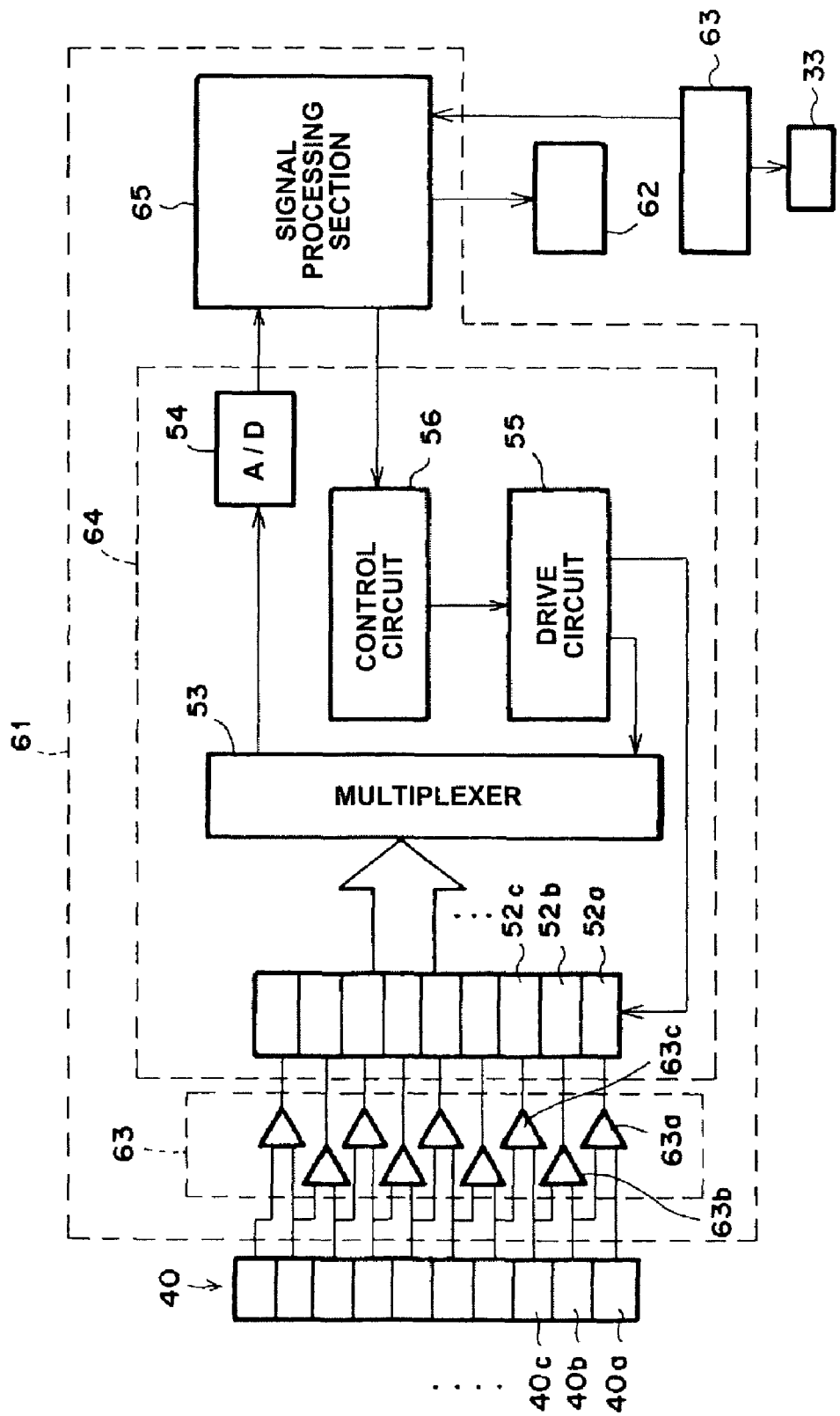
FIG. 7 is a block diagram of measurement means employed in the surface plasmon resonance sensor of FIG. 5.

Referring to FIG. 5 through FIG. 7, there is depicted a surface plasmon resonance sensor constructed in accordance with a second embodiment of the present invention. In the figures, the same reference numerals will be applied to the same parts as the first embodiment of FIG. 1 through FIG. 3. Therefore, a description of the same parts will not be given unless particularly necessary.

In addition to the parts of the first embodiment, the sensor of the second embodiment further includes a shutter 33 and a timing control section 63. The shutter 33 is used for controlling the irradiation of the light beam 30, while the timing control section 63 is used to cause measurement means 61 to make a measurement in synchronization with the timing at which the shutter 33 is opened.

The shutter 33, as shown in FIGS. 5 and 6, is provided between a light source 31 and a condenser lens 32. The light source 31 always emits a light beam 30. When the shutter 33 is in a closed state, the light beam 30 is shut off. When the shutter 33 is open, on the other hand, the light beam 30 is irradiated to the interface 12a of a measuring chip 10.

A controller 64 receives an address signal A which represents a position at which rotation of a turntable drive means 21 is stopped, from the turntable drive means 21. Based on a predetermined sequence, the controller 64 also outputs a drive signal D to actuate the turntable drive means 21. Furthermore, the controller 64 is equipped with measurement means 61 to which the output signal S from the aforementioned photodetector 40 is input; a display unit 62 to which an output signal from the measurement means 61 is input; and timing control section 63 for controlling the timing at which the shutter 33 is actuated and the timing at which the measurement means 61 makes a measurement.

During measurement, the timing control section 63 of the controller 64 opens the shutter 33 for a predetermined time so that the irradiation energy of the light beam 30 to be irradiated to the interface 12a of the measuring chip 10 is a predetermined value (e.g., 50 mJ/mm$^2$). The relationship between the irradiation of the light beam 30 to be irradiated to the interface 12a of the measuring chip 10 and the time during which the shutter 33 is open is previously measured and stored in the timing control section 63.

The timing control section 63 causes the measurement means 61 to perform measurement in synchronization with the timing at which the shutter 33 is opened. That is, as shown in FIG. 7, operation of the signal control section 66 of the measurement means 61 is controlled, and based on the light intensities received by the photodiodes 40a, 40b, 40c, . . . during the time the shutter 33 is open, the differentiated value I' output from the differential amplifier 63e is displayed on the display unit 62. Instead of controlling the signal control section 66, the differential amplifiers (63a, 63b, 63c, . . . ) or sample holding circuits (52a, 52b, 52c, . . . ) may be controlled to acquire the result of measurements synchronized with the opening operation of the shutter 33. Alternatively, if the photodetector 40 employs a CCD array instead of a photodiode array, the photodetector 40 may be exposed in synchronization with the opening operation of the shutter 33 so that detection signals synchronized with the opening operation of the shutter 33 are obtained.

As has been made clear from the description above, in addition to the advantages of the first embodiment, the second embodiment is capable of accurately controlling the irradiation energy of the light beam 30 that is irradiated to the interface 12a of the measuring chip 10. Furthermore, in the second embodiment, the detection of light intensity or measurement of ATR is performed in synchronization with the timing at which the light beam 30 is irradiated. As a result, detection signals during periods in which the light beam 30 is not irradiated can be prevented from having influence on the result of measurements as noise. Thus, the reliability of the measurement result is enhanced.

Figure 8:
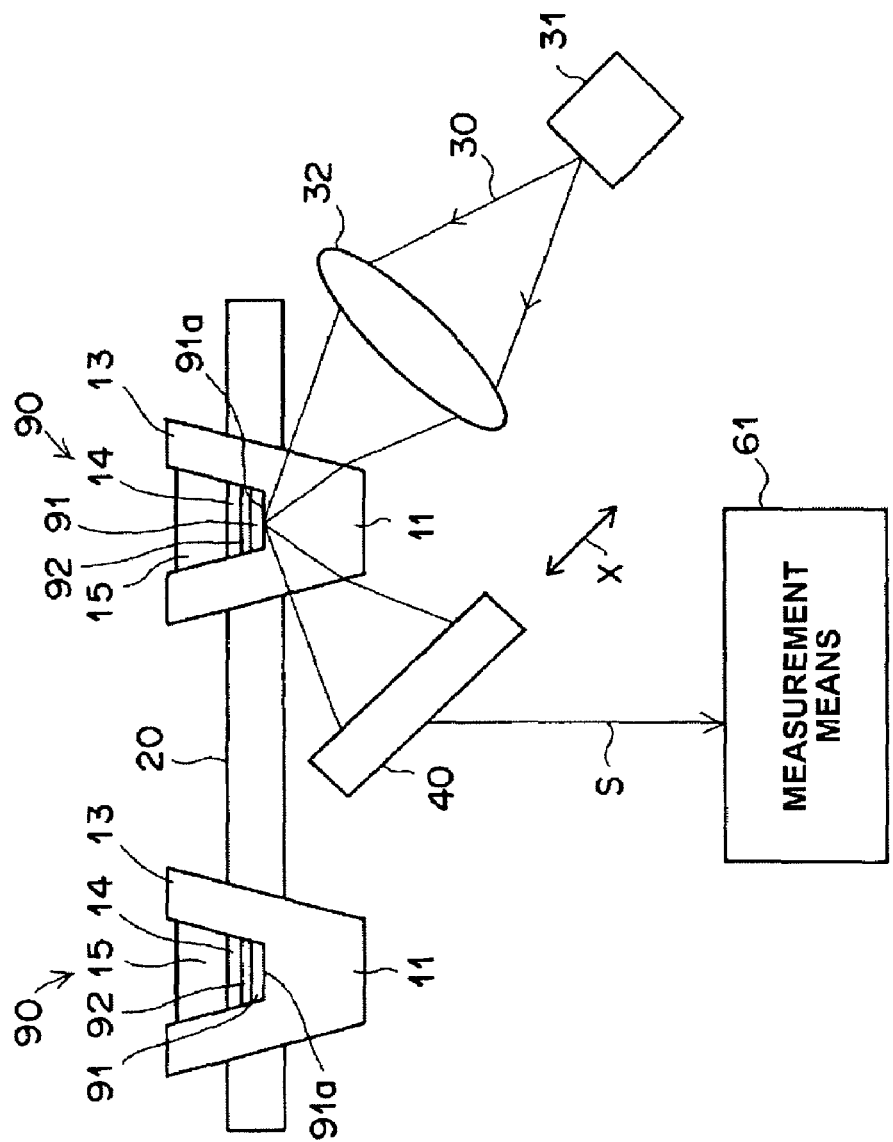
FIG. 8 is a side view showing a leaky mode sensor constructed in accordance with a third embodiment of the present invention.

A third embodiment of the present invention will be described with reference to FIG. 1 and FIG. 8. Since the third embodiment is nearly the same as the first embodiment of FIGS. 1 and 2, the parts of the third embodiment differing from the first embodiment of FIG. 2 are represented by different reference numerals (90, 92). In FIG. 8, the same reference numerals will be applied to the same parts as the first embodiment of FIG. 2. Therefore, a description of the same parts will not be given unless particularly necessary.

The sensor utilizing ATR according to the third embodiment is constructed as the aforementioned leaky mode sensor and employs a measuring chip 90. The measuring chip 90 is constructed of a dielectric block 11. The dielectric block 11 includes a cladding layer 91 formed on one surface (the top surface in the figure) thereof, and an optical waveguide layer 92 formed on the cladding layer 91.

The dielectric block 11 is formed, for example, from synthetic resin, or optical glass (BK7, etc). The cladding layer 91 is formed as a thin film by employing a dielectric or metal (such as gold, etc.) lower in refractive index than the dielectric block 11. The optical waveguide layer 92 is also formed as a thin film by employing a dielectric, which is higher in refractive index than the cladding layer 91, such as polymethylmethacrylate (PMMA). The thickness of the cladding layer 91 is 36.5 nm in the case where it is formed from a thin gold film. The thickness of the optical waveguide layer 92 is about 700 nm in the case where it is formed from PMMA.

In the leaky mode sensor of the above construction, when a light beam 30 emitted from a laser light source 31 strikes the cladding layer 91 through the dielectric block 11 at incidence angles greater than a critical angle at which total internal reflection (TIR) occurs, the light beam 30 is totally reflected at an interface 91a between the dielectric block 11 and the cladding layer 91. However, the light with a specific wave number, incident on the optical waveguide layer 92 through the cladding layer 91 at a specific incidence angle, propagates through the optical waveguide layer 92 in a waveguide mode. If the waveguide mode is excited in this manner, most of the incident light is confined within the optical waveguide layer 92, and consequently, ATR occurs in which the intensity of the light totally reflected at the interface 91a drops sharply.

The wave number of the light propagating through the optical waveguide layer 92 depends upon the refractive index of a sensing substance 14 on the optical waveguide layer 92. Therefore, the refractive index of the sensing substance 14 can be measured by finding the above-mentioned specific incidence angle $\theta_{sp}$ at which ATR takes place. In addition, based on a differentiated value I' which is a difference between values detected by adjacent photodiodes of the photodetector 40, a temporal change in the differentiated value, that is, a temporal change in the state of ATR is measured, whereby the state of the bond between the target substance and the sensing substance 14 can be measured.

In the third embodiment, as with the aforementioned embodiments, the laser light source 31 and the condenser lens 32 are configured so that when a measurement is made, the irradiation energy of the light beam at the interface 91a is 50 mJ/mm$^2$. Therefore, a change in refractive index of the liquid sample 15 resulting from a change in temperature of the liquid sample 15 due to irradiation of the light beam 30 is about 100, converted to molecular weight. Since the molecular weight of a target substance in the liquid sample 15 is 200 or greater, the state of the bond between the target substance and the sensing substance 14 can be accurately measured even if there is a change in refractive index of about 100, converted to molecular weight. Therefore, it can be judged whether there is a bond between the target substance and the sensing substance 14. That is, it can be accurately judged whether the target substance is a specific substance which bonds with the sensing substance 14. In addition to this advantage, the same advantages as the first embodiment can be obtained.

Figure 9:
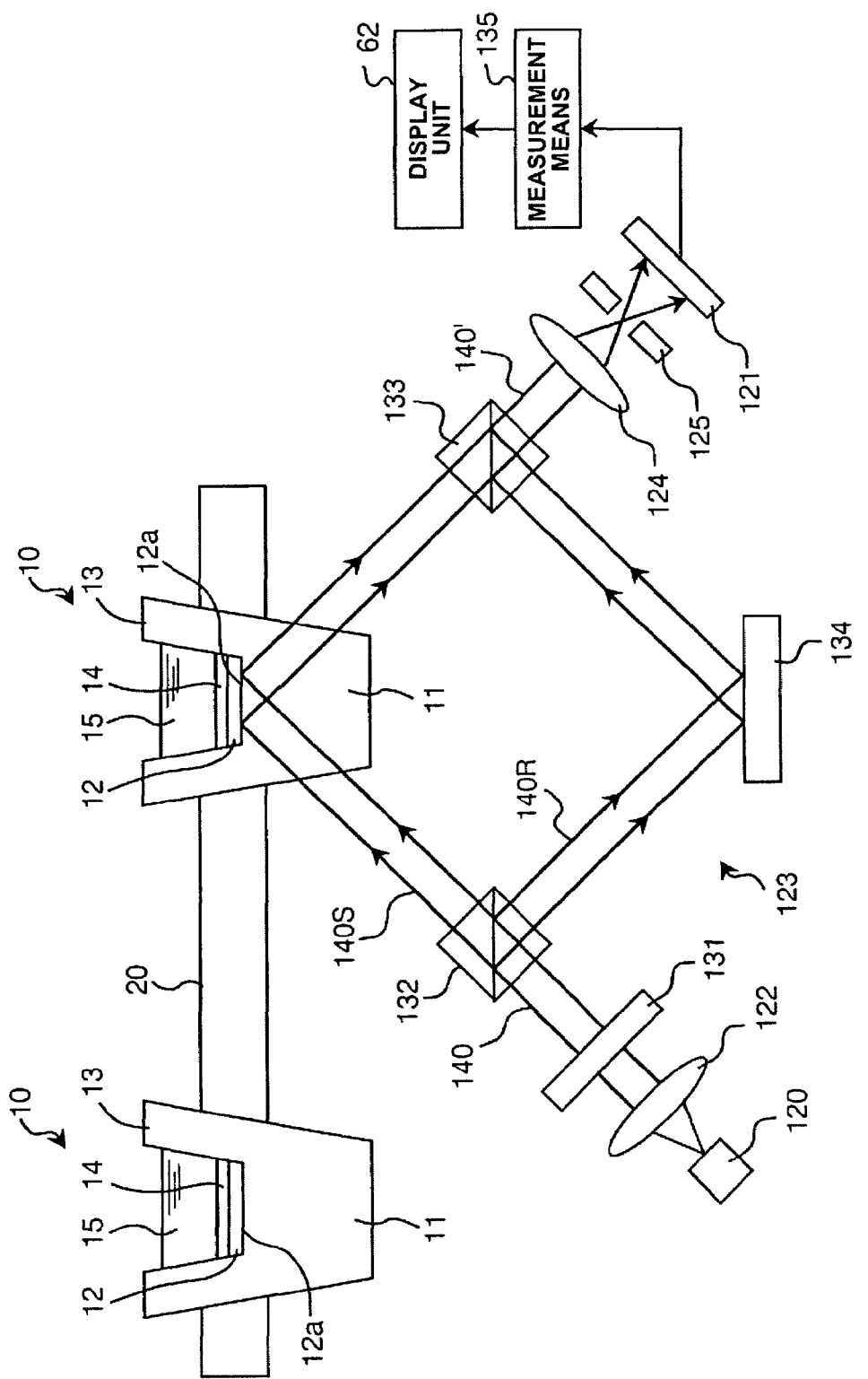
FIG. 9 is a side view showing a surface plasmon resonance sensor constructed in accordance with a fourth embodiment of the present invention.
Figure 10:
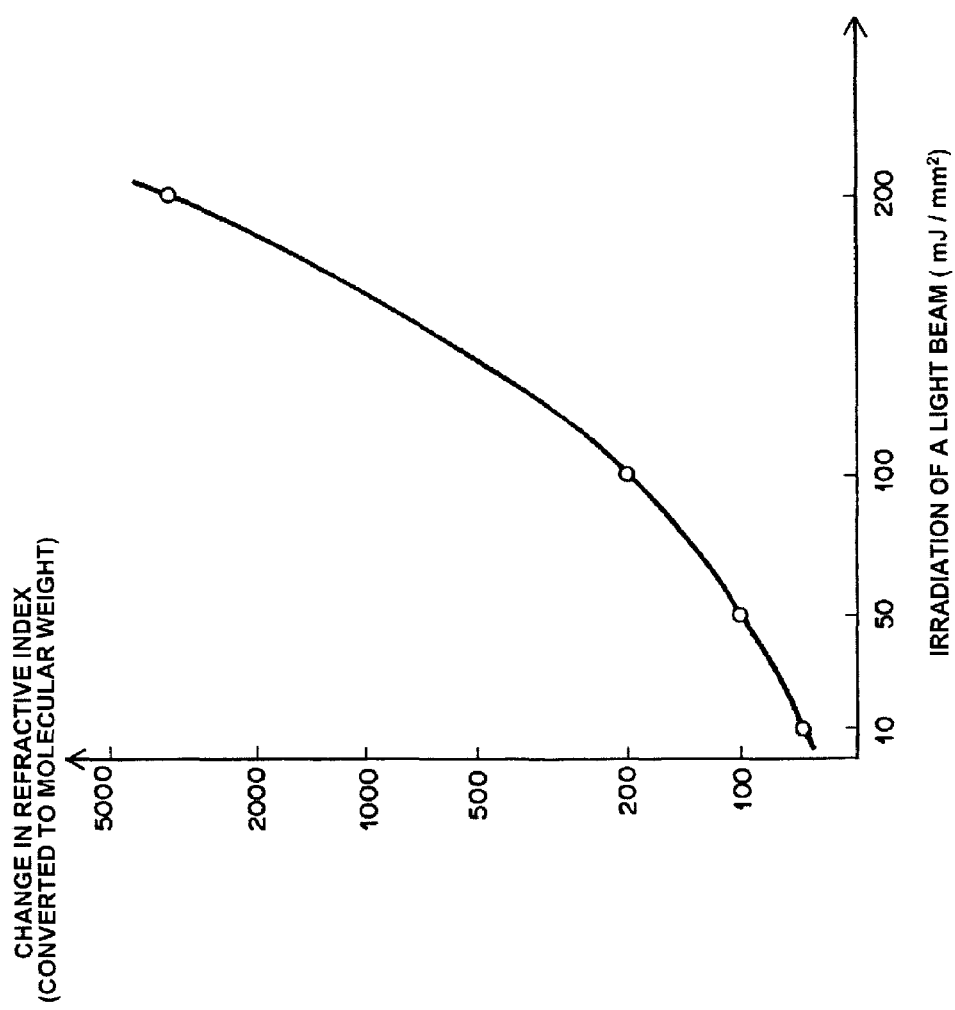
FIG. 10 is a diagram showing the relationship between the irradiation of a light beam and a change in refractive index.

Referring to FIG. 9, there is depicted a surface plasmon resonance sensor constructed in accordance with a fourth embodiment of the present invention. The surface plasmon resonance sensor of the fourth embodiment is the same in overall construction as that of the first embodiment shown in FIG. 1. However, the method of measurement in the fourth embodiment differs from that of the first embodiment.

As shown in FIG. 9, the surface plasmon resonance sensor of the fourth embodiment includes a laser light source 120 and a charge-coupled device (CCD) 121, which are disposed at measuring positions. The surface plasmon resonance sensor further includes a collimator lens 122, an optical interference system 123, a condenser lens 124, and an aperture plate 125, which are disposed between the laser light source 120 and the CCD 121.

The optical interference system 123 is constructed of a polarizing filter 131, a first half mirror 132, a second half mirror 133, and a third mirror 134. The CCD 121 is connected to measurement means 135, which is in turn connected to a display unit 62.

A description will hereinafter be given of how measurements are made by the surface plasmon resonance sensor of the fourth embodiment. The laser light source 121 is driven and emits a light beam 140 in a divergent state. The light beam 140 is collimated by the collimator lens 122 and is transmitted through the polarizing filter 131. The light beam 140 transmitted through the polarizing filter 131 strikes an interface 12a as a p-polarized light beam. The light beam 140 from the polarizing filter 131 is split into a reference light beam 140R and a light beam 140S by the first half mirror 132. The light beam 140S strikes the interface 12a. The light beam 140S, totally reflected at the interface 12a, and the reference light beam 140R, reflected at the mirror 134, are synthesized into a light beam 140' by the second half mirror 133. The synthesized light beam 140' is condensed by the condenser lens 124. The light beam 140' is passed through the aperture plate 125 and detected by the CCD 121. The light beam 140' detected by the CCD 121 produces interference fringes according to the state of the interference between the light beam 140S and the reference light beam 140R.

In the fourth embodiment, whether the sensing substance 14 fixed on the surface of the metal film 12 is a substance which bonds with a target substance in the liquid sample 15 can be judged by measuring the liquid sample 15 continuously after dropping of the liquid sample 15, and then detecting a change in the interference fringe detected by the CCD 121. That is, it can be judged by detecting a change in the interference fringe whether the target substance is a specific substance that bonds with the sensing substance 14.

That is, since the refractive index of the sensing substance 14 changes according to the state of the bond between the target substance in the liquid sample 15 and the sensing substance 14, the state of an interference fringe changes when the light beam 140S and the reference light beam 140R are synthesized by the half mirror 133. Therefore, a bonding reaction can be detected according to a change in the interference fringe. The measurement means 135 detects the above-mentioned reaction, based on the aforementioned principle. The result of detection is displayed on the display unit 62.

In the fourth embodiment, as with the aforementioned embodiments, the laser light source 120, condenser lens 122, polarizing filter 123, and half mirror 132 are configured so that when a measurement is made, the irradiation energy of the light beam at the interface 12a is 50 mJ/mm$^2$. Therefore, as in the first embodiment, it can be accurately judged whether there is a bond between the target substance and the sensing substance 14. That is, it can be accurately judged whether the target substance is a specific substance that bonds the sensing substance 14.

Finally, although the present invention has been described with reference to the preferred embodiments and modifications, the invention is not to be limited to the details given herein, but maybe modified within the scope of the invention hereinafter claimed.

What is claimed is:

1. A sensor utilizing attenuated total reflection, comprising:
    a light source for emitting a light beam;
    a measuring chip comprising
        a dielectric block transparent to said light beam, a thin film layer formed on one surface of said dielectric block, and a liquid-sample holding mechanism for holding a liquid sample on said thin film layer;
    an optical system for making said light beam enter said dielectric block at an angle of incidence so that a total internal reflection condition is satisfied at an interface between said dielectric block and said thin film layer;
    photodetection means for detecting intensity of said light beam totally reflected at said interface; and
    measurement means for measuring a state of attenuated total reflection, based on the result of detection obtained by said photodetection means;
    wherein irradiation energy of said light beam at said interface is 100 mJ/mm$_2$ or less.

2. The sensor as set forth in claim 1, wherein the irradiation energy of said light beam is 50 mJ/mm$^2$ or less.

3. The sensor as set forth in claim 2, wherein the irradiation energy of said light beam is 10 mJ/mm$^2$ or less.

4. The sensor as set forth in claim 1, wherein
    a sensing substance which interacts with said liquid sample is placed on said thin film layer, and
    said measurement means measures a temporal change in the state of attenuated total reflection, based on a plurality of detection results obtained at predetermined intervals by said photodetection means.

5. The sensor as set forth in claim 2, wherein
    a sensing substance which interacts with said liquid sample is placed on said thin film layer, and
    said measurement means measures a temporal change in the state of attenuated total reflection, based on a plurality of detection results obtained at predetermined intervals by said photodetection means.

6. The sensor as set forth in claim 3, wherein
    a sensing substance which interacts with said liquid sample is placed on said thin film layer, and
    said measurement means measures a temporal change in the state of attenuated total reflection, based on a plurality of detection results obtained at predetermined intervals by said photodetection means.

7. The sensor as set forth in claim 1, further comprising:
    a shutter disposed between said light source and said dielectric block; and
    timing control means for controlling the timing at which an operation of detection in said photodetection means is performed or the timing at which an operation of measurement in said measurement means is performed so that said operation is synchronized with an opening operation of said shutter.

8. The sensor as set forth in claim 2, further comprising:
    a shutter disposed between said light source and said dielectric block; and
    timing control means for controlling the timing at which an operation of detection in said photodetection means is performed or the timing at which an operation of measurement in said measurement means is performed so that said operation is synchronized with an opening operation of said shutter.

9. The sensor as set forth in claim 3, further comprising:
    a shutter disposed between said light source and said dielectric block; and
    timing control means for controlling the timing at which an operation of detection in said photodetection means is performed or the timing at which an operation of measurement in said measurement means is performed so that said operation is synchronized with an opening operation of said shutter.

10. The sensor as set forth in claim 4, further comprising:
    a shutter disposed between said light source and said dielectric block; and
    timing control means for controlling the timing at which an operation of detection in said photodetection means is performed or the timing at which an operation of measurement in said measurement means is performed so that said operation is synchronized with an opening operation of said shutter.

11. The sensor according to claim 1, wherein said optical system comprises a condenser lens.

12. The sensor according to claim 1, wherein said measurement means comprises:
    a differential amplifier array connected to the photodetection means;
    a driver holding outputs of the differential amplifier array and comprising a plurality of sample holding circuits; and
    a signal processing system.

13. The sensor according to claim 12, wherein said driver comprises:
    a plurality of holding circuits for holding outputs of a plurality of differential amplifiers of the differential amplifier array;
    a multiplexer to which is input outputs of the plurality of sample holding circuits;

an analog to digital converter digitizing an output of the multiplexer; and a drive circuit driving the multiplexer.

14. The sensor according to claim 1, wherein said photodetection means comprises a plurality of photodiodes juxtaposed in a row and disposed perpendicular to a travel direction of the light beam satisfying the total internal reflection condition.

15. The sensor according to claim 1, wherein said optical system comprises:

a polarizing filter;

a first half mirror; and a second half mirror.

16. The sensor according to claim 4, wherein the measurement means measures a reflected light intensity to detect a bond between a target substance and the sensing substance to determine whether the target substance in the liquid sample bonds with the sensing substance.

* * * * *